United States Patent [19]

Hocum

[11] Patent Number: 4,911,105
[45] Date of Patent: Mar. 27, 1990

[54] HARNESS FOR RESTRAINING A CHILD IN BED

[76] Inventor: Lois J. Hocum, 6224 Teller St., Arvada, Colo. 80003

[21] Appl. No.: 224,578

[22] Filed: Jul. 26, 1988

[51] Int. Cl.[4] .......... A61F 5/37; A61F 13/00
[52] U.S. Cl. .................... 119/96; 128/876; 128/875; 5/431
[58] Field of Search .............. 119/96, 29; 128/869–876; 2/44, 45; 182/3, 4; 224/257–259; 244/151 R; 272/70, 109; 294/140; 297/484; 5/431

[56] References Cited

U.S. PATENT DOCUMENTS

| | | | |
|---|---|---|---|
| 879,164 | 2/1908 | Hamilton | 128/134 |
| 1,310,958 | 7/1919 | O'Connor | 128/875 |
| 1,502,276 | 7/1924 | Siebert | 128/134 |
| 1,574,672 | 2/1926 | McCarroll-Doull | 128/134 |
| 1,779,337 | 10/1930 | Rowland | 128/134 |
| 2,034,954 | 3/1936 | Murphy | 128/134 |
| 2,432,392 | 7/1947 | Krogh | 128/134 |
| 2,456,898 | 12/1948 | Strandhagen | 128/134 |
| 2,486,114 | 10/1949 | Cataldo | 128/134 |
| 2,652,052 | 9/1953 | Smith | 128/134 |
| 2,675,557 | 4/1954 | Kempner, Jr. | 2/114 |
| 2,868,194 | 1/1959 | Lee | 128/134 |
| 3,099,486 | 7/1963 | Scott | 297/389 |
| 3,136,311 | 6/1964 | Lewis | 128/134 |
| 3,181,530 | 5/1965 | Storey | 128/134 |
| 3,301,594 | 1/1967 | Pukish, Jr. | 297/389 |
| 3,315,671 | 4/1967 | Creelman | 128/134 |
| 3,323,150 | 6/1967 | Rehder | 5/336 |
| 3,437,089 | 4/1969 | Posey | 128/134 |
| 3,536,067 | 10/1970 | Sternagel | 128/134 |
| 3,641,997 | 2/1972 | Posey, Jr. | 128/134 |
| 4,050,737 | 9/1977 | Jordan | 297/389 |
| 4,117,840 | 10/1978 | Rasure | 128/134 |
| 4,132,230 | 1/1979 | Ladd | 128/134 |
| 4,308,629 | 1/1982 | Freeman | 119/96 |
| 4,360,014 | 11/1982 | Manahan | 128/134 |
| 4,657,005 | 4/1987 | Williamson | 128/134 |
| 4,744,354 | 5/1988 | Triunfol | 128/875 |

OTHER PUBLICATIONS

"Ger Harness" Instruction Sheet, copyright 1983, DeRoyal Industries, Inc.

Primary Examiner—John Weiss
Attorney, Agent, or Firm—Sheridan, Ross & McIntosh

[57] ABSTRACT

A restraining device for holding a child in a bed. The device includes a body harness and hold down straps. The body harness is designed to permit the child to be placed either on his or her back, stomach or either side of the bed. Additionally, the hold down strraps are designed to lie flat against the bed. A lateral hold down strap is positioned so as to secure the child to the bed, yet permit the child to move its upper and lower extremities. The device is adjustable to comfortably and securably restrain children of various sizes.

18 Claims, 3 Drawing Sheets

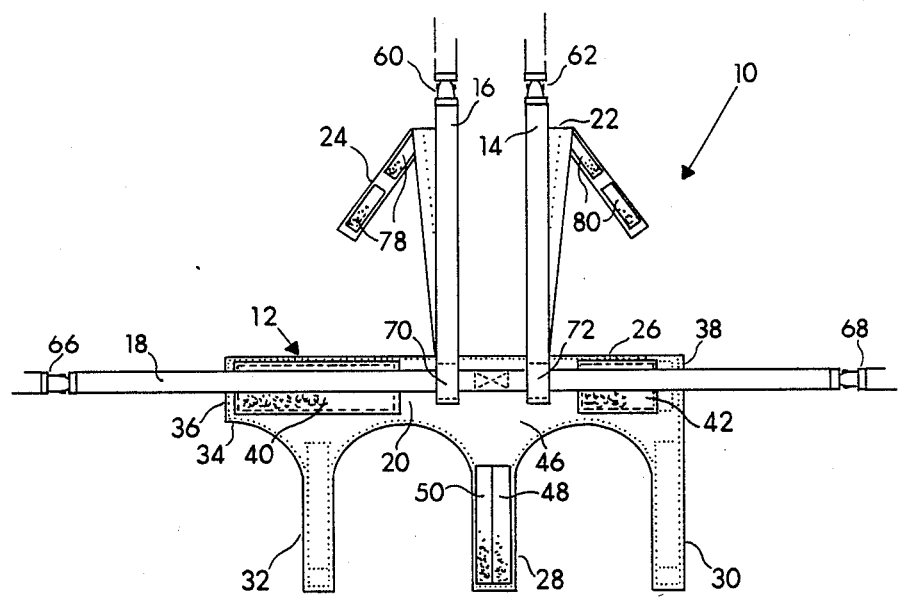
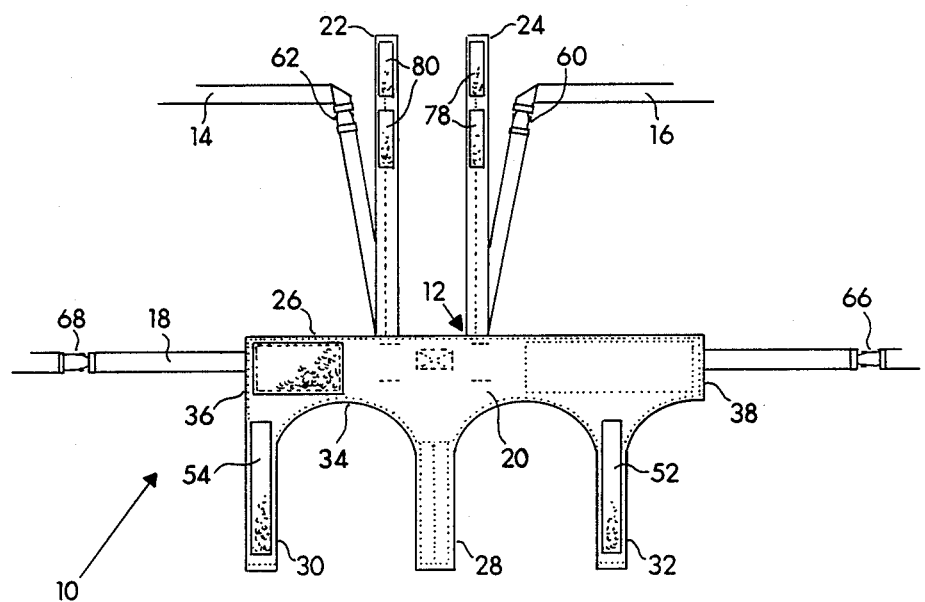

HARNESS FOR RESTRAINING A CHILD IN BED

FIELD OF THE INVENTION

The present invention relates to restraining harnesses, and more specifically to harnesses for restraining a child in bed.

BACKGROUND OF THE INVENTION

Restraining harnesses are well known. For example, U.S. Pat. No. 4,050,737 by Jordan, issued Sept. 27, 1977, discloses a harness for restraining a child in a chair. The harness comprises a back portion with upper and lower straps for fastening the harness to the backrest of a chair; laterally extending side flaps adapted to be wrapped around the side of a child's body between the armpits and the hips and across the chest and abdomen and secured together in overlapping relationship by releasable fastening means; and shoulder straps and a crotch strap. However, a harness employed to support a child in a chair may differ in many respects from one employed to restrain a child in a bed. Because a chair harness may be designed to restrain a person in a chair, to support a person in a sitting position or both, it necessary must function differently than a harness designed to hold an individual on a flat or inclined bed. For example, the placement of the straps may differ. Additionally, as shown in FIGS. 8, 9 and 10 of U.S. Pat. No. 4,050,737, support panels may be employed which would be inappropriate on a harness for use in a bed.

A garment for restraining a child in a bed is disclosed in U.S. Pat. No. 4,117,840 by Rasure, issued Oct. 3, 1978. The garment comprises a one-piece flexible body panel having an aperture for receiving the head of the wearer and body portions for wrapping around the torso of the wearer to form a jacket-like article of clothing. Restraining straps are connected to the upper portion of the garment near the neck aperture for attachment to the head of a bed, and to the lower portion of the garment near the waist, for attachment to the sides of the bed. The device disclosed in U.S. Pat. No. 4,117,840 suffers from a number of disadvantages. For example, the restraining straps which are adjacent the neck aperture do not lie flat against the bed. This may result in a child's head becoming entangled in the straps and the child possibly choking. The restraining straps adjacent the neck also restrict the degree to which the child may lift his or her head and shoulders. Additionally, the transverse restraining strap is connected to the garment near the child's waist. This restricts the child's ability to move the lower portion of the child's body. In many instances, it is advantageous for the child to move the upper and lower portions of his or her body in order that development of the muscles and bone structure as well as motor skills are not unduly retarded during the period of time the child is restrained in a bed. The disclosed device does not have a crotch strap. Therefore, a child may slip downwardly in the garment, resulting in possible injury, such as by choking on the neck aperture. Furthermore, a child placed in a garment of this type can only lie upon his or her back. There are no provisions for positioning the child on his or her stomach or on either side.

Medical Restraints Inc. of Knoxville, Tenn. 37918, manufactures a device designed for infants afflicted with gastroesophageal reflux (GER). This device secures the infant to a bed in a prone position on his or her abdomen. The device is illustrated in a brochure entitled "GER Harness," copyright 1983. One problem with the harness is that the restraining straps do not lie flat upon the bed. This can lead to possible entanglement of the child with the straps causing choking or other serious bodily harm.

U.S. Pat. No. 4,657,005 by Williamson, issued Apr. 14, 1987, also discloses a harness designed for infants afflicted with GER. It is claimed that this harness has a number of advantages over the GER harness marketed by Medical Restrains Inc. of Knoxville, Tenn. However, this harness only permits placement of the child on his or her abdomen. The harness does not allow the child to be secured to a bed while resting on his or her back or on either side. Additionally, the transverse restraining strap disclosed in U.S. Pat. No. 4,657,005 is located near the waist of the child, thereby unduly restricting beneficial movement of the lower portion of the child's body during the period of restraint. Furthermore, the upper restraining straps are located near the shoulders and restrict movement of the child's upper body.

In light of the shortcomings of prior art child restraining devices, it would be advantageous to have a device which allows a child to be restrained in a bed, yet permits relatively free movement of the upper and lower portions of the child's body. This would permit the child to move his or her arms, head, shoulders, legs, hips and lower trunk so as to aid proper physical development. Alternatively, if the child is placed in traction, it is sometimes necessary to have the lower trunk elevated. Prior art devices which have restraining straps at the waist can prevent adequate elevation and interfere with proper positioning for traction. Additionally, it would be advantageous if the restraining device permits the child to be selectively restrained in various positions, such as on his or her back, stomach, or either side with the head of the bed elevated from about 0° to about a 45° angle. Furthermore, it would be advantageous if the restraining straps lie flat against the bed, to reduce chances of the child becoming entangled in the straps. It would be advantageous if the restraining straps and/or the entire harness are quickly releasable in the event of an emergency. Further, it would be advantageous if the body harness to be worn by the child is adjustable to accommodate children of various sizes. It would also be advantageous if the device is easily washable.

SUMMARY OF THE INVENTION

The present invention involves a device for restraining a child in a bed, stretcher or the like. The bed can be flat or elevated, for example up to about 45°. The device includes a body harness which encircles the trunk of the child, preferably from the hip region to just below the armpits. The body encircling portion preferably has a first and second end which can be wrapped around the child and fastened together. Crotch straps extend from the lower edge of the body encircling portion of the body harness. Shoulder straps extend from the upper edge of the body encircling portion. Upper hold down straps for attaching to the head of a bed extend from the back of the body harness. A lateral hold down strap for attaching to the sides of a bed extends from the back of the body encircling portion.

Preferably, at least two loops are provided on the back of the body encircling portion through which the lateral hold down strap may be selectively passed. Devices designed to be used on larger children, for example children weighing over 10 pounds, preferably have four loops. If all loops are engaged by the lateral hold down strap, the harness can be positioned to lie flat against the bed surface. A child may be placed either face down or face up in the harness, thereby permitting positioning of the child on the back or stomach. Alternatively, if only the loop or loops on one side of the harness are engaged by the lateral hold down strap, the child may be positioned on one of his or her sides. By engaging only the loop or loops on the other side, the child may be positioned on his or her other side. Preferably, the lateral hold down strap is located just below the armpits of the child in order to permit the child to move the lower portion of his or her body and to stabilize the trunk against lateral movement. The upper restraining straps are preferably attached to the middle of the back of the body encircling portion, rather than at the shoulders, to allow the child to move his or her head and shoulders.

The device of the present invention provides a number of important advantages over prior art devices. It permits a child to be restrained on a bed and yet allows for the positioning of a child on either his or her stomach, back or either side. Additionally, the hold down straps are designed to lie flat against the bed in order to reduce chances of the child becoming entangled in the hold down straps. Furthermore, the body harness is adjustable to different sizes in order to be used on infants and small children of various sizes. The device of the present invention also permits the child to freely move the upper and lower portions of his or her body while restrained on the bed. This provides important therapeutic functions or alternatively provides for proper positioning of a child in traction. The present device has a number of applications, including use with children having cleft lip repairs, cranial surgery or injuries, respiratory infections, GER, airway anomalies or skeletal traction.

BRIEF DESCRIPTION OF THE DRAWINGS

FIG. 2 is a plan view of the device shown in FIG. 1 open to flat form.

FIG. 3 is a plan view of the opposite side of the device shown in FIG. 2.

DETAILED DESCRIPTION OF THE INVENTION

Figure 1:
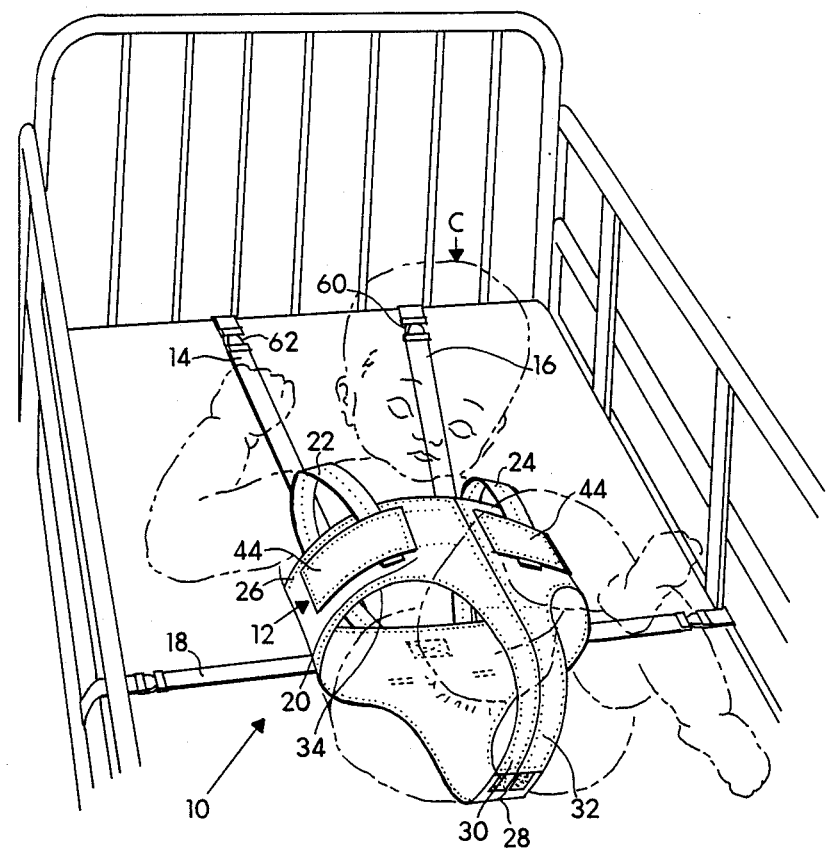
FIG. 1 illustrates an embodiment of the device of the present invention in use restraining a child, drawn in phantom, on his or her back in a bed.

A preferred embodiment of the device of the present invention will be described with reference to FIG. 1. The restraining device 10 includes a body harness 12, upper restraining straps 14 and 16, and a lateral restraining strap 18. The body harness 12 includes a trunk encircling portion 20. Shoulder straps 22 and 24 extend from the upper edge 26 of the body encircling portion 20. Crotch straps 28, 30 and 32 extend from the lower edge 34 of the body encircling portion 20.

Referring now to FIG. 2 which shows the restraining device 10 in flat form. The side of the device 10 shown in FIG. 2 is the side which faces away from the body of a child placed in the device 10. The body encircling portion 20 of the body harness 12 has two ends 36 and 38. When the body encircling portion 20 is wrapped around a child C, the two ends 36 and 38 are releasably fastened to one another in an overlapping relationship (See FIG. 1). Preferably the devices for fastening the two ends are contact fasteners such as the type of fastening closures comprised of fabric tapes having naps or piles formed of myriad small fiber loops and fiber hooks. For purposes of the present invention, this type of fastening device shall be referred to as "hook and loop fabric fastener." Such material is commercially available and is marketed under the trademark "Velcro." While this type of material can conveniently be used, the present device is not limited thereto. Fasteners 40 and 42 are placed on the ends 36 and 38 of the body encircling portion 20 so as to permit size adjustment in order to accommodate children of various sizes. Exposed portions of the hook-type fasteners (e.g. 40 and 42) can be covered with a loop-type patch 44 (see FIG. 4) in order to prevent contact between the child's skin or clothing and the somewhat abrasive hooks. It will be appreciated that if hook and loop fabric fasteners are employed, fastener 40 does not have to be a hook type fastener. For example, 42 can be the hook type and 40 can be the loop type.

The crotch straps of the present invention preferably comprise first, second and third crotch straps 28, 30 and 32 respectively. The first crotch strap 28 extends from the lower edge 34 of the back 46 of the body encircling portion 20. For purposes of the present description, the back portion 46 will be that portion of the body harness 12 which contacts the bed when a child using the device 10 is lying on his or her back or stomach. It will be understood that the back portion 46 does not necessarily correspond to the back of a child placed in the device 10 because the child may be placed either face down or face up in the device 10. Therefore, the back portion 46 may contact either the back or the stomach of the child placed in the device 10. The second crotch strap 30 extends from the lower edge 34 of the body encircling portion 20 near the first end 36. The third crotch strap 32 extends from the lower edge 34 near the second end 38 of the body encircling portion 20 of the body harness 12.

Figure 4:
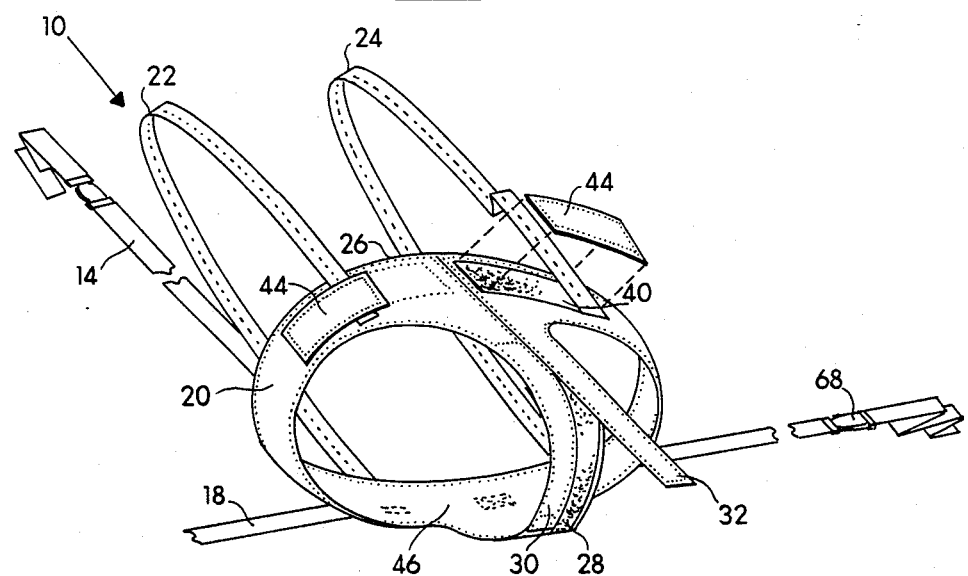
FIG. 4 illustrates the device shown in a partially interconnected position.

In a preferred embodiment, the first crotch strap 28 extends between the thighs of the child from one direction, and the second and third crotch straps 30 and 32 extend between the thighs of the child from the opposite directiohn. The second and third crotch straps 30 and 32 are releasably fastened to the first crotch strap 28, preferably by contact fastening devices such as hook 48 and 50 and loop 52 and 54 (See FIG. 3) fabric fasteners. By employing the two crotch straps 30 and 32 (e.g. the second and third crotch straps) at the front of the body encircling portion 20, important advantages are provided. For example, when a relatively small infant is placed within the harness, the first 36 and second 38 ends of the body encircling portion 20 will overlap to such a degree that the second and third crotch straps 30 and 32 will be substantially overlapping. This will result in front crotch straps 30 and 32 with a relatively narrow total effective width. However, as progressively larger children wear the device, the first and second ends 36 and 38 will overlap progressively less. This will result in the second and third crotch straps 30 and 32 being offset more and more relative to one another, resulting in a wider total effective width for the front crotch straps 30 and 32. This increases both the ability of the harness 12 to secure the child as well as improves the comfort of the child. This is best illustrated in FIG. 4 where the second crotch strap 30 is shown connected to the first crotch strap 28. The third crotch strap 32 is shown positioned just prior to connection with first crotch strap 28. As illustrated, the third crotch strap 32 will slightly overlap the second crotch strap 30. If the ends of the body encircling portion 20 were overlapped more (i.e. for a child with a smaller waist), the crotch straps 30 and 32 would overlap more. Less overlap of the ends of the body encircling portion 20 (i.e. for use on a larger child) will result in less or no overlap of the second and third crotch straps 30 and 32.

As can be seen in FIGS. 2 and 3, the crotch straps 28, 30 and 32 are flared slightly at the top where they extend from the lower edge 34 of the body encircling portion 20. In this way, the crotch straps 28, 30 and 32 will fit more comfortably about the legs of the child using the device 10. Additionally, as can be seen in FIG. 2, the contact fasteners on the first crotch strap 28 are two separate longitudinal tapes 48 and 50. By employing two separate tapes 48 and 50 rather than a single tape, the first crotch strap 28 will fold more readily, therefore providing better comfort for the child wearing the device 10.

As can be seen most clearly in FIGS. 2 and 3, the upper hold down straps 14 and 16 each includes a releasable fastening devices 60 and 62. The lateral hold down strap 18 includes two releasable fastening devices 66 and 68. These releasable fastening devices are employed to releasably attach the ends of the hold down straps to the bed and are preferably quick release devices. The upper hold down straps 14 and 16 are releasably attached to the head of the bed. The two free ends of the lateral hold down strap 18 are releasably attached to the respective sides of the bed.

An important preferred feature of the present device 10 are loops 70 and 72 shown in FIG. 2. Although it is not necessary, it is preferred that these loops are formed from the lower ends of the upper hold down straps 14 and 16 at their points of attachment to the back 46 of the body encircling portion 20 of the body harness 12. The lateral hold down strap 18 is selectively engageable with each of these two loops. Alternatively, a greater number of loops can be employed. For example, in a device designed to be used with larger children, four loops can be employed instead of two.

Figure 5:
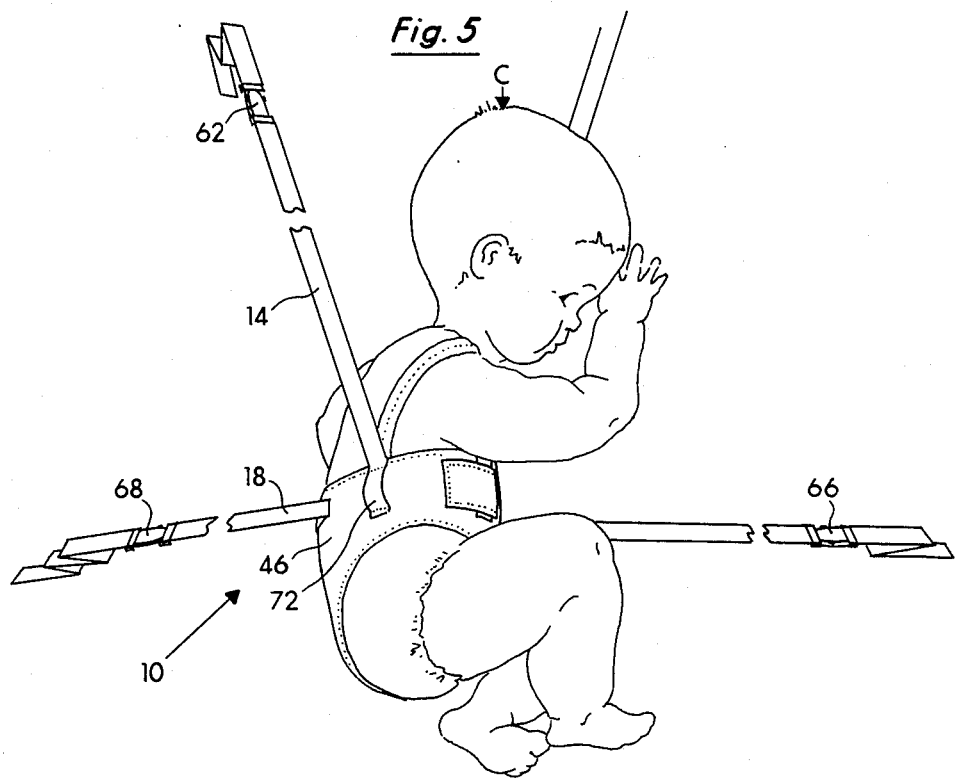
FIG. 5 illustrates the device with a child in one side.

When it is desired to hold the body harness 12 flat against a bed (as shown in FIG. 1), both loops 70 and 72 are engaged by the lateral hold down strap 18. Alternatively, if it is desired to position the child on his or her side, only one loop would be engaged. This is illustrated in FIG. 5 where lateral hold down strap 18 is shown not engaging loop 72, while loop 70 (not shown) is engaged. The position of the child on its side in FIG. 5 has been exaggerated to illustrate this feature. In actual use, the left arm and should would not be under the child and the right shoulder would only be slightly elevated off the bed. In other words, the child would be more nearly positioned on his or her back, and the straps 14 and 18 would be more nearly flat against the bed. An important advantage of such a position is that the child is substantially prevented from resting on side of his or her head against the bed. Thus a child with cranial surgery or an injury on one side of his or her head can be positioned to substantially prevent that side of the head from contacting the bed.

As shown in FIG. 3, the two shoulder straps 22 and 24 include releasable fastener devices, preferably of the hook and loop fabric type 78 and 80. These can be adjustably attached to mating pieces 40 and 42 (See FIG. 2) on the body encircling portion 20. In this manner, the shoulder straps are adjustable to accommodate children of various sizes. The body encircling portion 20, the two shoulder straps 22 and 24 and the crotch straps 28, 30 and 32 all work in concert to restrain a child securely within the body harness 12. The upper hold down straps 14 and 16 and the lateral hold down strap 18 restrain the body harness 12 securely against the bed. However, because of the preferred placement of the lateral hold down strap 18 near the armpit region of the child and the upper hold down straps 14 and 16 on the back 46, the child is able to move the upper and lower portions of his or her body without undue restriction. This is illustrated in FIG. 1 where the child C is shown lifting his or her legs, arm and head. As discussed hereinbefore, this provides important therapeutic advantages for the child.

The body harness of the present invention can be constructed of a variety of materials. Materials can include natural materials such as denim, synthetic materials or combinations of the two. Padding can be placed between the material used to construct the harness in order to provide for the comfort of the child. As will be appreciated by those skilled in the art, releasable fastening means other than hook and loop fabric fasteners can be employed. It is preferred that the fabric employed in the construction of the body harness be preshrunk. In this manner, when the device is washed, the fastening devices and the fabric harness will not shrink at differential rates, and bunching of the fabric around the fastening devices can be avoided.

The hold down straps can be constructed of any strong material. Flat materials are preferred in that bumps will not be produced, which can produce pressure spots against the child using the device 10. Releasable devices for connecting the hold down straps to the bed can be any type, but child-proof quick release devices are preferred. By providing both easily releasable devices of the hold down straps as well as releasable fasteners on the harness, in case of an emergency, the child can be removed by either disconnecting the hold down straps from the bed or alternatively releasing the child from the harness. This is an important safety feature.

The device of the present invention is adjustable to accommodate children of various sizes. The device is preferably used on newborn to about 2 year old children. Preferably, a smaller device is used on children up to 10 pounds, and a larger device is used on children weighing more than 10 pounds.

While various embodiments of the present invention have been described in detail, it is apparent that modifications and adaptations of those embodiments will occur to those skilled in the art. However, it is to be expressly understood that such modifications and adaptations are within the spirit and scope of the present invention, as set forth in the following claims.

What is claimed is:

1. A device for holding a child on a bed comprising:
    (1) a body harness member comprising a lateral body encircling portion having a back portion, an upper edge and a lower edge, two shoulder straps extending from said upper edge and crotch strap means extending from said lower edge;
    (2) at least one upper hold down strap for attaching to the head of said said bed extending from said back of said lateral body encircling portion of said body harness;

(3) a lateral hold down strap having two ends, wherein each end may be connected to a side of said bed, said lateral hold down strap being fastenable to the back portion of said lateral body encircling portion of said body harness so that said lateral hold down strap is substantially just below the armpit level of a child placed in said device;

wherein a child may be placed within said device with the back of said child contacting the back portion of said body harness member thereby permitting the child to rest on a bed lying on his or her back and wherein a child may be placed in said device with his or her stomach facing said back portion of said body harness member thereby allowing said child to rest on his or her stomach on said bed.

2. The device of claim 1 wherein said lateral body encircling portion of said body harness further comprises first and second end portions and wherein when said device is in use, the first and second end portions wrap around the child and are releasably fastenable to one another.

3. The device of claim 1 wherein said lateral hold down strap is attached to said body harness member approximately in the middle of said back portion of said body encircling portion.

4. The device of claim 2 wherein said crotch strap means comprises:
  (1) a first crotch strap extending from the lower edge of said back portion of said body encircling portion of said body harness member;
  (2) a second crotch strap extending from the lower edge of said body encircling portion near said first end; and
  (3) a third crotch strap extending from the lower edge of said body encircling portion near said second end;
  wherein said first crotch strap extends between the child's thighs from a first direction and said second and third straps extend between the child's thighs from a second direction and said first strap is releasably fastenable to said second and third straps to secure the child within said body harness.

5. The device of claim 4 wherein said first crotch strap member includes releasable fastener means comprising one-half of a hook and loop type fabric fastener and wherein said hook or loop portion of said fastener means comprises two separate longitudinal tapes secured to said first strap member.

6. The device of claim 2 wherein said first end of said body encircling portion of said body harness is releasably attached to said second end by means of a hook and loop type fabric fastener means and further wherein exposed hook portions are covered by separate pieces of loop fastener material in order to prevent contact between the child and hook portions of the fastener means.

7. The device of claim 1 wherein said upper hold down strap for connecting to the head of the bed and said lateral hold down strap for connecting to the sides of the bed lie flat against the bed when in use in order to minimize the chances of a child becoming entangled in said hold down straps.

8. The device of claim 1 wherein said hold down straps further comprise child-proof quick release fastener means to provide for the connection of said hold down straps to said bed.

9. The device of claim 1 wherein said lateral body encircling portion of said body harness encircles the child's body substantially from below the child's armpits to the child's hips.

10. The device of claim 1 wherein said body harness is constructed of a washable, preshrunk fabric.

11. A device for holding a child on a bed comprising:
  (1) a body harness member comprising a back portion, two side portions, a front portion, shoulder straps and crotch strap means;
  (2) at least two upper hold down straps connected to the back portion of said body harness for securing the harness to the head of a bed; and
  (3) a lateral hold down strap fixably connected to a central back portion of said body harness and connectable to the sides of a bed;
  wherein said back portion of said body harness further includes at least two loops which are selectably engageable by said lateral hold down strap;
  wherein a first of said loops is located laterally to the left of the point at which said lateral hold down strap is fixably connected and a second of said loops is located laterally to the right of the point at which said lateral hold down strap is fixably connected;
  wherein when said first and second loops are both engaged by said lateral hold down strap, the back portion of said body harness is secured to the bed in a manner to permit a child to be placed either on his or her back or his or her stomach; and
  wherein when only a loop or loops located laterally to one side of the point at which said lateral hold down strap is fixably connected to said body harness member are engaged by said lateral hold down strap, a child placed in the body harness will rest more on the corresponding side of his or her body than the other side.

12. The device of claim 11 wherein two of said loops are formed from the lower ends of said upper hold down straps.

13. A device for holding a child on a bed comprising:
  (1) a body harness including a lateral position having first and second ends and an upper edge and a lower edge;
  (2) a first crotch strap extending from the middle lower edge of said lateral portion;
  (3) a second crotch strap extending from the lower edge of one end of said lateral portion;
  (4) a third crotch strap extending from the lower edge of a second end of said lateral portion;
  (5) hold down straps extending from the back of said lateral portion for connection with the head of a bed; and
  (6) a lateral hold down strap for connecting to the sides of a bed;
  wherein said first crotch strap is releasably engageable with said second and third crotch straps and wherein said first end of said lateral portion is releasably engageable with said second end of said lateral portion.

14. The device of claim 13 wherein said body harness further comprises shoulder straps extending from the upper edge of said lateral portion.

15. The device of claim 13 wherein said first crotch strap includes releasable fastening means comprising one-half of a hook and loop type fastener and further wherein said fastening means comprises two longitudinal hook or loop fastener tapes located side by side on said first crotch strap.

16. A device for holding a child on a bed comprising:
(1) a body harness member comprising a lateral body encircling portion having a back portion, an upper edge and a lower edge and a first end and a second end, shoulder straps extending from said upper edge and crotch strap means extending from said lower edge;
(2) at least one upper hold down strap for attaching to the head of said bed extending from said back portion of said lateral body encircling portion of said body harness;
(3) a lateral hold down strap having two ends, wherein each end may be connected to a side of said bed, said lateral hold down strap being fastenable to the back portion of said lateral body encircling portion of said body harness so that said lateral hold down strap is substantially just below the armpits of a child placed in said device;
wherein said crotch strap means comprises:
  (i) a first crotch strap extending from the lower edge of said back portion of said lateral body encircling portion of said body harness member;
  (ii) a second crotch strap extending from the lower edge of said lateral body encircling portion near said first end; and
  (iii) a third crotch strap extending from the lower edge of said lateral body encircling portion near said second end;
wherein said first crotch strap includes releasable fastener means comprising one-half of a hook and loop type fabric fastener and wherein said hook or loop portion of said fastener means comprises two separate longitudinal tapes secured to said first crotch strap; and
wherein said back portion of said body harness further includes at least two loops which are selectively engageable by said lateral hold down strap.

17. A device for holding a child on a bed comprising:
(1) a body harness member comprising a lateral body encircling portion having a back portion, an upper edge, a around the child and are releasably fastenable to one another; and
(2) crotch strap means extending from said lower edge, said crotch strap means comprising:
  (a) a first crotch strap extending from the lower edge of said back portion of said body encircling portion of said body harness member;
  (b) a second crotch strap extending from the lower edge of said body encircling portion near said first end; and
  (c) a third crotch strap extending from the lower edge of said body encircling portion near said second end;
wherein said first crotch strap extends between the child's thighs from a first direction and said second and third straps extend between the child's thighs from a second direction and said first strap is releasably fastenable to said second and third straps to secure the child within said body harness.

18. The device of claim 17 wherein said first crotch strap includes releasable fastener means comprising one-half of a hook and loop type fabric fastener and wherein said hook or loop portion of said fastener means comprises two separate longitudinal tapes secured to said first strap member.

* * * * *

UNITED STATES PATENT AND TRADEMARK OFFICE
CERTIFICATE OF CORRECTION

PATENT NO. : 4,911,105

DATED : March 27, 1990

INVENTOR(S) : Lois J. Hocum

It is certified that error appears in the above-identified patent and that said Letters Patent is hereby corrected as shown below:

Title page:

In the Abstract, line 5, delete "strraps" and insert therefor --straps--.

Column 1, lines 24 and 25, delete "necessary" and insert therefor --necessarily--.

Column 2, line 10, delete "Restrains" and insert therefor --Restraints--.

Column 3, line 50, delete "in" and insert therefor --on--.

Column 4, line 16, delete "the".

Column 4, line 47, delete "directiohn" and insert therefor --direction--.

Column 5, line 55, delete "should" and insert therefor --shoulder--.

Column 5, line 61, delete "on" and insert therefor --one--.

Column 6, line 41, delete "of" and insert therefor --on--.

UNITED STATES PATENT AND TRADEMARK OFFICE
CERTIFICATE OF CORRECTION

PATENT NO. : 4,911,105

DATED : March 27, 1990

INVENTOR(S) : Lois J. Hocum

It is certified that error appears in the above-identified patent and that said Letters Patent is hereby corrected as shown below:

Column 7, line 42, delete "froma" and insert therefor --from a--.

Column 10, line 9, after "a" insert --lower edge, and first and second end portions, wherein when said device is in use, the first and second end portions wrap--.

Column 10, line 14, delete "portionof" and insert therefor --portion of--.

Signed and Sealed this

Fifth Day of March, 1991

Attest:

HARRY F. MANBECK, JR.

*Attesting Officer*     *Commissioner of Patents and Trademarks*